(12) United States Patent
Jessop et al.

(10) Patent No.: US 8,075,307 B2
(45) Date of Patent: Dec. 13, 2011

(54) POLYMERIZABLE TEMPORARY COATING METHODS AND SYSTEMS FOR INTRAORAL DEVICES

(75) Inventors: Neil T. Jessop, Sandy, UT (US); Richard D. Tuttle, Layton, UT (US)

(73) Assignee: Ultradent Products, Inc., South Jordan, UT (US)

( * ) Notice: Subject to any disclaimer, the term of this patent is extended or adjusted under 35 U.S.C. 154(b) by 524 days.

(21) Appl. No.: 12/237,194

(22) Filed: Sep. 24, 2008

(65) Prior Publication Data

US 2009/0087809 A1 Apr. 2, 2009

Related U.S. Application Data

(60) Provisional application No. 60/976,253, filed on Sep. 28, 2007.

(51) Int. Cl.
*A61C 13/225* (2006.01)
*A61K 6/08* (2006.01)
(52) U.S. Cl. ............................ 433/24; 433/180; 523/120
(58) Field of Classification Search .................. 523/120; 433/24, 180
See application file for complete search history.

(56) References Cited

U.S. PATENT DOCUMENTS

| | | | | |
|---|---|---|---|---|
| 3,081,177 A * | 3/1963 | Garay et al. | ................ | 106/38.51 |
| 3,445,420 A * | 5/1969 | Kookootsedes et al. | ...... | 524/862 |
| 4,362,842 A | 12/1982 | Masuhara et al. | | |
| 4,559,013 A | 12/1985 | Amstutz et al. | | |
| 4,978,391 A * | 12/1990 | Jones | .............................. | 106/35 |
| 5,078,596 A | 1/1992 | Carberry et al. | | |
| 5,112,640 A * | 5/1992 | Warunek et al. | ............. | 427/2.24 |
| 5,160,260 A | 11/1992 | Chang | | |
| 5,179,186 A * | 1/1993 | Muller et al. | .................. | 528/49 |
| 5,403,885 A | 4/1995 | Voigt et al. | | |
| 5,513,987 A * | 5/1996 | Hosoi et al. | ................ | 433/168.1 |
| 5,575,644 A | 11/1996 | Tuneburg | | |
| 5,810,582 A | 9/1998 | Doyle | | |
| 5,876,208 A | 3/1999 | Mitra et al. | | |
| 6,660,204 B1 * | 12/2003 | Clover et al. | ................. | 264/222 |
| 6,685,921 B2 * | 2/2004 | Lawlor | ............................ | 424/49 |
| 7,182,596 B2 | 2/2007 | Paulus | | |
| 7,807,730 B2 * | 10/2010 | Bissinger et al. | ............. | 523/113 |
| 2003/0145863 A1 * | 8/2003 | Fischer et al. | ................ | 128/862 |
| 2006/0073434 A1 | 4/2006 | Reynolds | | |
| 2006/0084024 A1 | 4/2006 | Farrell | | |
| 2006/0172247 A1 | 8/2006 | Abels et al. | | |
| 2007/0122362 A1 * | 5/2007 | Giniger et al. | .................. | 424/53 |

FOREIGN PATENT DOCUMENTS

| | | |
|---|---|---|
| JP | 02023956 | 1/1990 |
| JP | 05194860 | 8/1993 |
| NL | 8900876 | 4/1989 |
| WO | 2006122081 | 11/2006 |

\* cited by examiner

*Primary Examiner* — Tae H Yoon
(74) *Attorney, Agent, or Firm* — Workman Nydegger

(57) ABSTRACT

Methods and systems for temporarily coating intra-oral devices (e.g., orthodontic brackets and/or wires) so as to reduce discomfort to soft tissues within a patient's mouth. One embodiment of such a system includes at least one orthodontic bracket or orthodontic arch wire and a two-part polymerizable temporary coating composition for use in coating selected surfaces of the brackets and/or wires. One silicone polymerizable two-part composition includes a vinyl siloxane component, a cross-linking component, and a catalyst activator initially divided between the two parts so that at least one of the components is kept separate from at least one other component (i.e., all three components are not initially commingled). Upon mixing of the first and second parts, the composition begins to polymerize.

28 Claims, 2 Drawing Sheets

POLYMERIZABLE TEMPORARY COATING METHODS AND SYSTEMS FOR INTRAORAL DEVICES

RELATED APPLICATIONS

The present application claims the benefit of U.S. Patent Application Ser. No. 60/976,253, filed Sep. 28, 2007, entitled "POLYMERIZABLE TEMPORARY COATING METHODS AND SYSTEMS FOR INTRAORAL DEVICES", the disclosure of which is incorporated by reference in its entirety.

BACKGROUND OF THE INVENTION

1. The Field of the Invention

The present invention relates to intraoral device systems, for example orthodontic bracket systems for use in correcting spacing and orientation of the teeth.

2. The Relevant Technology

Orthodontics is a specialized field of dentistry that involves the application of mechanical forces to urge poorly positioned, or crooked, teeth into correct alignment and orientation. Orthodontic procedures can be used for cosmetic enhancement of teeth, as well as medically necessary movement of teeth to correct overjets or overbites. For example, orthodontic treatment can improve the patient's occlusion, or enhanced spatial matching of corresponding teeth.

The most common form of orthodontic treatment involves the use of orthodontic brackets and wires, which together are commonly referred to as "braces." Orthodontic brackets, more particularly the orthodontic bases, are small slotted bodies configured for direct attachment to the patient's teeth or, alternatively, for attachment to bands which are, in turn, cemented or otherwise secured around the teeth. Once the brackets are affixed to the patient's teeth, such as by means of glue or cement, a curved arch wire is inserted into the slot of each bracket. The arch wire acts as a template or track to guide movement of the teeth into proper alignment.

The bracket bases are formed of a rigid material, typically metal, ceramic, or a rigid plastic in order to withstand the forces transferred to the bracket from the arch wire during treatment. The arch wires used are also typically formed of metal (e.g., stainless steel or nickel-titanium). When fitting a patient with an orthodontic bracket system, the hard, rigid orthodontic brackets and/or wires can often irritate the soft, sensitive tissues of the mouth. This is particularly so at the beginning of treatment and when any adjustments are made, as after a short time the tissues of the mouth become somewhat calloused, reducing the discomfort or pain caused by the presence of the brackets and/or wires.

In order to help alleviate the discomfort, soft wax is used in an attempt to coat portions of the brackets and/or wires during the early stages of treatment and after adjustments are made, so as to soften the contact surfaces between the patient's mouth and the brackets and/or wires. Although it typically only takes a few days to a couple of weeks for the mouth tissues to callous and adjust to the presence of the braces, the soft wax material is easily displaced after minutes or no more than a couple hours, which is usually not long enough to be effective at reducing discomfort. The easy displacement of the soft wax requires the patient to frequently reapply the wax coating or to accept the discomfort and pain, neither of which are desirable. As such, it would be an improvement in the art to provide alternative systems and methods for temporarily coating portions of the orthodontic bracket system so as to reduce discomfort. Such improvements would also be useful with other intra-oral devices (e.g., removable partial dentures or bridges, palette expanders, or other devices used within the oral cavity), the use of which can often result in pain and discomfort to the patient as a result of contact between the devices and the soft, sensitive tissue within the oral cavity.

BRIEF SUMMARY OF THE PREFERRED EMBODIMENTS

The present invention is directed to systems and methods for use in temporarily coating intra-oral devices (e.g., orthodontic brackets and/or arch wires) so as to reduce the discomfort to soft tissues within a patient's mouth. One embodiment of such a system includes at least one intra-oral device and a two-part polymerizable composition for use in coating selected surfaces of the intra-oral devices (e.g., to coat select surfaces of one or more of the brackets and/or the arch wire(s) of an orthodontic system). Various two-part polymerizable compositions which result in a relatively soft, flexible polymerized composition may be employed, for example a two-part silicone composition. Although silicone is preferred, soft, flexible polymerizable compositions based on polyurethanes and/or epoxies may also provide a suitable soft, flexible polymerized composition. Preferably the two parts of any such polymerizable composition are of relatively high viscosity so as to have a moldable, putty like consistency.

In a preferred embodiment, the two-part polymerizable composition comprises a two part silicone composition in which a first part of the two-part silicone composition includes a vinyl siloxane component and a cross-linking component, while a second part includes a catalyst activator. Upon mixing of the first and second parts, the composition begins to polymerize. The vinyl siloxane component, the cross-linking component, and the catalyst activator may be arranged within the first and second parts of the composition differently than described above, so long as all three components are not placed together (as this begins the polymerization reaction).

In one embodiment, the first and second parts are advantageously of relatively high viscosity so that two parts having a putty-like consistency are dispensed onto, for example, a patient's finger tips and then rolled and/or kneaded together so as to result in good mixing of the two parts. In one embodiment, the putty-like composition is moldable (e.g., clay-like and/or similar to silly putty), and may be substantially dry to the touch (i.e., non-sticky). Furthermore, the composition may further include a flavorant and/or a colorant. Including colorants within one or both parts of the composition provides each part with an initially different color so that as they are rolled and kneaded together, there is a visual indication as to when mixing is substantially complete. Inclusion of a flavorant is particularly beneficial as the composition is applied within the patient's mouth. The flavorant provides a more palatable taste to the composition.

Another embodiment of the invention relates to a method of using such a two-part polymerizable composition to provide a temporary coating over desired surfaces of one or more intra-oral devices, such as orthodontic brackets and/or wires. Advantageously, the composition adheres or otherwise attaches to the applied surface for a period of time sufficient to allow the tissues within the mouth to adjust to the presence of the brackets and wires, and which advantageously wears off shortly after such an adjustment has occurred. For example, the first and second parts of the polymerizable temporary coating composition are mixed together (e.g., by rolling and/or kneading), after which the mixed composition is applied over selected surfaces of the brackets and/or wires installed within the patient's mouth. A highly viscous putty-like composition allows the patient to further shape, mold, and impress the material over brackets, archwires, or other intra-oral devices before and/or after placement so as to achieve a comfortable result that minimizes pokes and abrasions caused by the brackets, wires, or other intra-oral device. As the material begins to polymerize, it can be placed where needed over the brackets and/or wires. The composition completes the polymerization process in place, which provides an added benefit as the material adheres to or mechanically interlocks with the brackets and/or wires as a result of the in-situ polymerization process. As a result of the in-situ polymerization, the silicone material is not so easily displaced as wax, which is rubbed away much more easily.

All else being equal, the composition advantageously remains where applied significantly longer than wax. For example, if under a given set of circumstances wax may wear away within a few minutes to about an hour, the present compositions will remain in place significantly longer under similar conditions. For example, in typical usage, the present compositions may remain where applied for a period of at least about 8 hours, more typically at least about 1 day, and more typically at least about 2 days. Of course, the activities engaged in by the user will affect how long the composition remains in place before wearing away and/or becoming dislodged.

Of course, the actual time will depend on the activities engaged in by the user (e.g., resting, sleeping, eating, drinking, smoking), and activities which contact, abrade or otherwise wear away the temporary coating composition can be expected to decrease the actual time that the composition remains in place. In any case, all other things being equal, the temporary coating compositions of the present invention will provide significantly increased wear times as compared to traditionally used wax. The increased resistance to wear of the present temporary coating compositions require fewer applications (in some cases a single application may be sufficient) to allow the inner soft tissues of the oral cavity to callous and adjust to the presence of the orthodontic brackets, wires, or other intra-oral device, after which the polymerizable temporary coating composition is no longer needed. Advantageously the composition will simply wear away after the above typical lengths of time as a normal result of the movement of the tongue, the action of saliva, and other forces within the mouth (e.g., after no more than about 3-5 days), so that no affirmative step of removing the coating composition is needed. This is in contrast to various appliance covers which may fit over an intra-oral device (e.g., an orthodontic bracket), which are relatively bulky, and which must be actively removed by the patient once the inner soft tissues of the oral cavity have adjusted to the presence of the intra-oral device if the patient no longer wants the added bulk of the cover. The present temporary coating compositions greatly simplify and reduce the necessary actions required of the user.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

Figure 1:
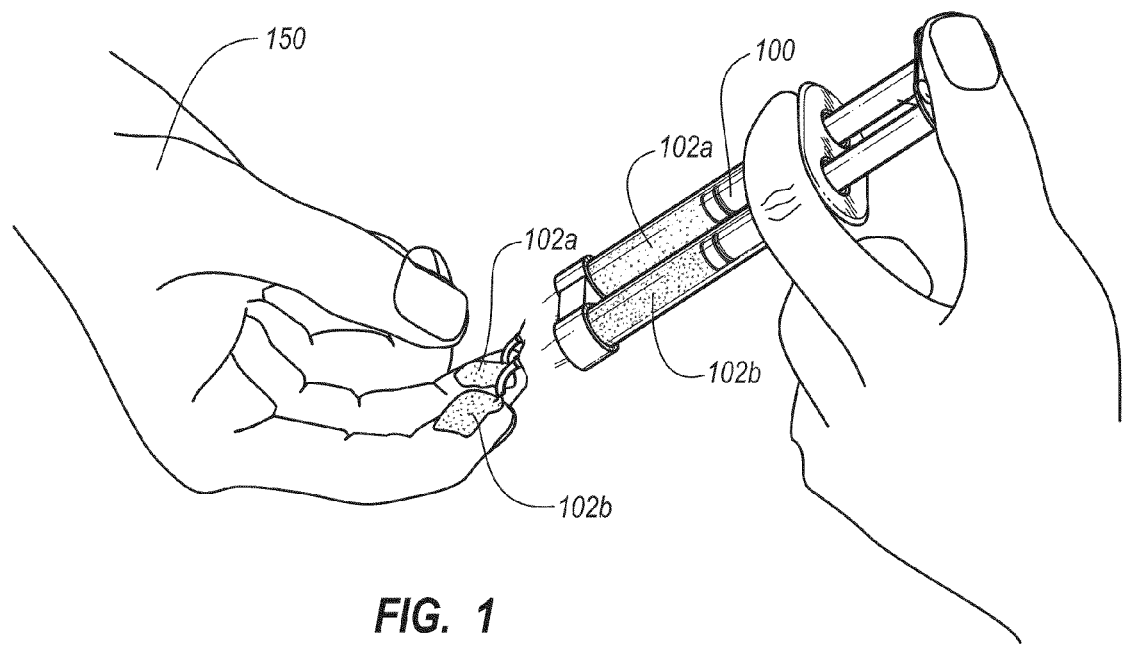
FIG. 1 is a perspective view showing a two-part polymerizable composition comprising two separate parts of putty-like consistency being dispensed onto the fingertips of a person.

The present invention is directed to methods and systems useful in temporarily coating intra-oral devices so as to reduce the discomfort to soft tissues within a patient's mouth. One embodiment of such a system may include at least one intra-oral device and a two-part polymerizable composition for use in coating selected surfaces of the intra-oral device. One class of intra-oral devices to which the invention is believed to be particularly applicable is in temporarily coating orthodontic appliances (e.g., orthodontic brackets and/or arch wires). Other intra-oral devices that may also benefit from the present invention include, but are not limited to, removable partial dentures (e.g., often formed of rigid metal or plastic), removable bridges, palette expanders, and even broken or otherwise rough dentures. For example, a porcelain denture or other appliance may become broken or otherwise rough, the discomfort from which may be alleviated by the present temporary coating compositions.

Various two-part polymerizable compositions which result in a relatively soft, flexible polymerized composition may be employed, for example a two-part silicone composition. Although silicone is preferred, soft, flexible polymerizable compositions based on polyurethanes and/or epoxies may also provide a suitable soft, flexible polymerized composition. Preferably the two parts of any such polymerizable composition are of relatively high viscosity so as to have a moldable, putty like consistency that will hold its shape absent application of a force (e.g., kneading/rolling). Such a putty likewise does not readily and quickly assume the shape of a container into which it is placed (as opposed to a liquid). It may be difficult to accurately measure the viscosity of a putty because of the incorporation of air bubbles within the material, although it is believed that the putty may typically have a viscosity between about 1 kPa-sec and about 1000 kPa-sec, more preferably between about 10 kPa-sec and about 500 kPa-sec and most preferably between about 25 kPa-sec and about 300 kPa-sec. The consistency and viscosity of the composition is largely determined by the molecular weight of the polymerizable components used to form the composition as well as the fraction and characteristics of fillers incorporated within the composition. Generally, increasing molecular weight of the polymerizable component(s) increases the viscosity of the composition. Increased filler contents also increase viscosity.

In the case of silicone, the two-part composition includes a vinyl siloxane component, a cross-linking component, and a catalyst activator (e.g. platinum). The vinyl siloxane component, the cross-linking component, and the catalyst activator may be arranged within the first and second parts of the composition in various configurations, so long as all three components are not placed together (as this begins the polymerization reaction). For example, the catalyst activator may be present within one part, while the cross-linking component is present within the other part, and the vinyl siloxane component may be divided so as to be present within both parts.

Upon mixing of the first and second parts, the composition begins to polymerize, which typically takes from about 10 seconds to about 3 minutes. As the material begins to polymerize, it can be placed where needed over the brackets and/or wires such that the silicone completes the polymerization process in place. Completion of polymerization in place allows the material to adhere to the intra-oral device and/or create a mechanical interlock (i.e., the material may be molded and shaped so as to overhang and mechanically grip or interlock with the underlying substrate) as a result of in-situ polymerization, which allows it to not be so easily displaced as wax, which is more easily rubbed away.

II. Exemplary Polymerizable Temporary Coating Compositions and Systems

Any two-part polymerizable composition suitable for placement and polymerization within the oral cavity may be used. Examples of such compositions include silicones, polyurethanes and/or epoxies that are soft, flexible, and moldable both before and after polymerization. A preferred class of compositions are polyvinyl siloxane silicones which polymerize through an addition-type chemistry. For example, with these materials, polymerization is carried out on siloxane components terminated with vinyl groups, which are also cross-linked during polymerization with another siloxane component that includes hydrogen atoms capable of cross linking with the vinyl siloxane component. The polymerization reaction is activated by a platinum catalyst.

In one embodiment, a first part of the two-part silicone composition includes the cross-linking component and at least a portion of the vinyl siloxane component, while a second part includes a catalyst activator (e.g., platinum) and optionally a portion of the vinyl siloxane component (e.g., the vinyl siloxane component typically comprises the largest fraction by weight of the three necessary components, and so it may be preferable to divide this component between the two parts so as to maintain an approximate mass or volumetric 1:1 ratio between the two parts). Exemplary vinyl siloxanes may include any suitable siloxane compound which includes at least two ends terminated with reactive vinyl groups. One preferred vinyl siloxane compound is dimethyl siloxane (DMS), whose generic structure is shown below.

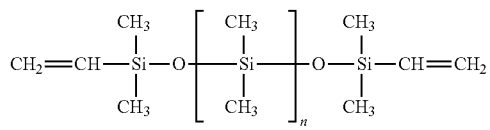

The letter n represents an integer, whose value (as well as the molecular weight of the DMS) may be selected so as to alter the viscosity and/or the polymerization time of the composition. The average molecular weight of the DMS is preferably between about 10,000 and about 1 million, more preferably between about 15,000 and about 500,000, and most preferably between about 25,000 and about 300,000. Unless specified otherwise, all molecular weights expressed herein are averages and expressed in Daltons. It is believed that putty-like consistency of alternative polymerizable temporary coating compositions (e.g., urethane or epoxy based) may be achieved with other polymerizable components (e.g., urethanes and/or epoxies) having molecular weights within similar ranges as described above, as well as by adjusting the filler content of any such compositions.

The vinyl siloxane is preferably included within the two-part composition in a range of about 20 to about 99 percent by weight, more preferably about 25 to about 75 percent by weight, and most preferably about 35 to about 65 percent by weight. In one embodiment, the vinyl siloxane may be present within both the first and second parts of the composition. The above described dimethyl siloxane is one example of a vinyl siloxane material that has been found to provide excellent physical properties including a viscosity characterized as putty-like in which the composition is easily moldable, as well as polymerization time characterized as providing sufficient time for a user to mold and press the material into place before polymerization is substantially complete, although various other vinyl siloxane materials may be selected based on these desired properties.

The two-part silicone composition also includes a cross-linking siloxane component, which cross links with the vinyl siloxane component during polymerization. Any siloxane co-polymer capable of cross-linking may be used, an example of which is methylhydrosiloxane dimethylsiloxane, whose structure is shown below.

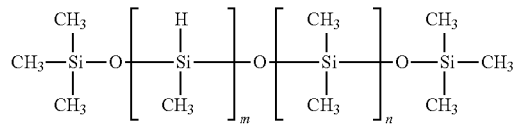

The H bonded to the silicon within the left side bracket reacts with a vinyl group of the vinyl siloxane (e.g., DMS), resulting in a cross-linked polymerized structure once polymerization is complete. The cross-linked structure provides additional strength to the polymerized material. The letter m represents an integer of at least two, whose value may be selected so as to alter the degree to which the polymerized material is cross linked, as well as the viscosity and/or the polymerization time of the composition. The letter n also represents an integer (which may be different than m, and may be different from the value of n within the DMS structure described above). The value of n within the cross-linking component may be selected so as to alter the viscosity and/or the polymerization time of the composition.

Molecular weight of the cross-linking component is preferably between about 100 and about 100,000, more preferably between about 1000 and about 10,000, and most preferably between about 2000 and about 5000. In one embodiment, the values of m and n are approximately equal. For example, the cross-linking component used within Example 1 below has values of m and n of about 25, and a molecular weight of about 3500. Generally, increasing the value of m and/or n (thus increasing molecular weight) increases the viscosity of the material prior to polymerization. The inclusion of fillers and what fraction of the composition they comprise also affect the viscosity of the material prior to polymerization; generally, increasing filler concentration increases viscosity. Thus, there is an interaction between molecular weights of the vinyl siloxane component, the cross linking component, and filler characteristics and content, all of which may be adjusted to provide a desired consistency and viscosity to the composition.

The siloxane cross-linking component is preferably included within the composition in a range of about 0.5 to about 10 percent by weight, more preferably about 1 to about 8 percent by weight, and most preferably about 2 to about 4 percent by weight. In embodiments in which the cross-linking component is included within a single part, the siloxane cross-linking component is preferably included within the one part of the composition in a range of about 1 to about 20 percent by weight, more preferably about 2 to about 15 percent by weight, and most preferably about 4 to about 8 percent by weight.

One or both parts of the two-part polymerizable temporary coating composition may also include one or more fillers. Exemplary fillers may include, but are not limited to a bulk glass particle filler, a fine silica filler, polyethylene and/or other polymer fillers (e.g., crushed), metal particles, aluminum oxide, silicon dioxide, titanium dioxide, and combinations thereof. One or more of the fillers may be silanated to improve adhesion and consistency within the material. In other words, the silanated, surface modified fillers are more easily coated and/or wetted by the other constituents within the composition. In one particularly preferred embodiment, each part of the composition includes both a bulk glass particle filler (e.g., having an average particle diameter in a range of about 0.5 and about 1 micron), as well as a fine silica filler (e.g., having an average particle diameter in a range of about 40-80 nm). The bulk glass particle filler increases viscosity and adds bulk and strength to the material, while the fine silica filler acts to adjust the viscosity and to improve the handleability of the material. Any included fillers are preferably included within the two part composition in a range of about 20 to about 70 percent by weight, more preferably about 30 to about 60 percent by weight, and most preferably about 40 to about 55 percent by weight. Any included fine silica filler (preferably silanated) preferably accounts for about 2 percent to about 10 percent by weight of the composition. All else being equal, when using higher molecular weight polymerizable components, the fraction of filler incorporated within the composition may be lower to achieved a desired viscosity and vice versa.

A plasticizing agent may also be included (e.g., glycerin), which acts to alter the consistency of the part or parts in which it is included, as well as the consistency of the polymerized composition. Any included plasticizing agents (e.g., glycerin) are preferably included within the two part composition in a range of about 0.1 to about 10 percent by weight, more preferably about 0.25 to about 4 percent by weight, and most preferably about 0.5 to about 2 percent by weight.

In the case of a silicone composition, the two-part composition includes a catalyst activator (e.g., platinum) which acts as a polymerization initiator. An example of a platinum catalyst is a platinum-divinyltetramethylsiloxane complex, although other platinum catalysts will be apparent to one of skill in the art. The catalyst activator is preferably included within the composition in a range of about 0.005 to about 1 percent by weight, more preferably about 0.01 to about 0.25 percent by weight, and most preferably about 0.025 to about 0.1 percent by weight of the composition. According to one embodiment, all of the catalyst activator is included within one part (e.g., the second part). As mentioned above, the second part of the two-part composition may also include a portion of the vinyl siloxane component, one or more fillers, and glycerin or another plasticizing agent. The concentration of the catalyst activator may be increased or decreased to alter the polymerization time of the composition (e.g., in order to decrease polymerization time, catalyst concentration may be increased). In the case of alternative systems (e.g., polyurethane or epoxy based), the concentrations of the components of the chemical initiator system may similarly be adjusted to alter the polymerization time of the composition.

The two-part composition may also include a flavorant and/or a colorant. Flavorants are preferably included within the composition in a range of about 0.01 to about 3 percent by weight, more preferably about 0.1 to about 2 percent by weight, and most preferably about 0.5 to about 1 percent by weight of the composition. Bubblegum is one particularly preferred flavorant. Other flavorants that may be used include, but are not limited to, grape, vanilla, mint, peach, almond, wintergreen, strawberry, cherry, and combinations thereof.

Colorants are preferably included within the composition in sufficient quantity to provide a visible color to one or both parts of the two part composition. Providing at least one part with a visible color aids in mixing of the two parts as it provides a visual indication as to when mixing has been accomplished. (i.e., there are no longer two distinct colored portions). This is particularly useful with a putty-like high viscosity composition, as mixing is accomplished by rolling and/or kneading the two parts of the composition together. Any color or combination of colors may be used. For example, one part may be colorless, while the other part may include any desired color. In another embodiment, each part may be of a different color either by natural coloring of the components or by addition of a colorant. Exemplary colorants include, but are not limited to red, green, blue, orange, white, tan, yellow, pink, and combinations thereof. Colorants may typically be included in a range of about 0.005 to about 1 percent by weight, more preferably about 0.01 to about 0.5 percent by weight, and most preferably about 0.05 to about 0.1 percent by weight of the composition.

The two-part composition may also include an anti-microbial component. The presence of such a component may help to prevent the growth of microbes around the intra-oral device(s), which is a common problem in patients receiving such treatments. Exemplary anti-microbial components that may be used include, but are not limited to, chlorhexidine, benzalkonium chloride, silver, and combinations thereof. Silver is particular preferred, as powders or particles comprising silver and capable of releasing therapeutic silver ions within the mouth may be easily incorporated within one or both parts of the two-part composition. An anesthetic agent may also be included, examples of which include, but are not limited to phenolic components (e.g., eugenol), benzocaine, lidocaine, prilocaine, and combinations thereof, which agents further aid in reducing any discomfort caused by the intra-oral device abrading against soft oral tissue. An anti-cariogenic component (e.g., fluoride) may also be present. When present, any anti-microbial components may typically be included within a range between about 0.01% to about 5% by weight of the composition, more preferably between about 0.1% to about 2% by weight, and most preferably between about 0.2% to about 1% by weight of the composition. Likewise, any anesthetic components may typically be included within a range between about 0.01% to about 5% by weight of the composition, more preferably between about 0.1% to about 2% by weight, and most preferably between about 0.2% to about 1% by weight of the composition.

With the preferred silicone composition, it is important that the cross-linking agent, the vinyl siloxane, and the catalyst activator advantageously not be present all within a single part of the two-part composition so as to prevent premature polymerization. In other words, polymerization requires the presence of all three of these components. Any scheme to divide these components may be employed, e.g., the catalyst may be maintained separate from the cross-linking component, with the vinyl siloxane component preferably present within both parts of the composition. In another example, the catalyst and the cross-linking component may be present within one part in which the vinyl siloxane is absent, and the vinyl siloxane may be present in the second part (in which the other two components are absent). Other optional components (e.g., fillers, plasticizers, flavorants, colorants, antimicrobials, anesthetics, anti-cariogenics) may be present within either or both parts of the two-part composition.

III. EXAMPLES

Example 1

An exemplary two part silicone composition was formed from the following components. All percentages are by weight, unless specified otherwise.

| Part One | |
|---|---|
| DMS (MW 28,000) | 50.0% |
| Methylhydrosiloxane dimethylsiloxane cross-linker (MW 3500) | 6.0% |
| Silanated 0.7 micron glass filler | 37.5% |
| Silanated nano silicone filler | 5.5% |
| Glycerin | 1.0% |
| Part Two | |
| DMS (MW 28,000) | 50.0% |
| Silanated 0.7 micron glass filler | 42.9% |
| Silanated nano silicone filler | 6.0% |
| Glycerin | 1.0% |
| Platinum-divinyltetramethylsiloxane complex | 0.1% |

The two parts were of relatively high viscosity so as to have a putty like consistency and were kneaded and rolled together for about 30 seconds so as to effect mixing of the two parts. The mixed composition was applied over a labial surface of a selected orthodontic bracket bonded to a tooth before polymerization was complete, and was shaped and molded to a desired shape and coverage of the bracket. The composition completed polymerization within about 80 seconds after initial mixing, which polymerization was completed in place on the bracket. The polymerized composition had a soft, rubbery feel, and adhered to and/or mechanically interlocked around the bracket so as to clasp and grip the bracket surface, preventing rubbing of the bracket surface against the soft inner labial tissue of the orthodontic patient. The composition remains in place significantly longer than wax, and wears away and/or becomes dislodged in normal use after about 8 hours to about 2 days.

Example 2

An exemplary two part silicone composition is formed from the following components. All percentages are by weight, unless specified otherwise.

| Part One | |
|---|---|
| DMS (MW 28,000) | 50.0% |
| Methylhydrosiloxane dimethylsiloxane cross-linker | 6.0% |
| Silanated 0.7 micron glass filler | 37.5% |
| Silanated nano silicone filler | 5.5% |
| Glycerin | 1.0% |
| Part Two | |
| DMS (MW 28,000) | 50.0% |
| Silanated 0.7 micron glass filler | 40.9% |
| Silanated nano silicone filler | 6.0% |
| Glycerin | 1.0% |
| Platinum-divinyltetramethylsiloxane complex | 0.1% |
| Bubblegum flavor | 2% |

The two parts are of relatively high viscosity so as to have a putty like consistency and are kneaded and rolled together for about 30 seconds so as to effect mixing of the two parts. The mixed composition is applied over a labial surface of a selected orthodontic bracket bonded to a tooth before polymerization is complete, and is shaped and manipulated to a desired shape and coverage of the bracket. The composition completes polymerization within about 80 seconds after initial mixing, which polymerization is completed in place on the bracket. The polymerized composition has a soft, rubbery feel, and adheres to and/or mechanically interlocks around the bracket so as to grip the bracket surface, preventing rubbing of the bracket surface against the soft inner labial tissue of the orthodontic patient. The composition has a bubblegum flavor and remains in place significantly longer than wax, and wears away and/or becomes dislodged in normal use after about 8 hours to about 2 days.

Example 3

An exemplary two part silicone composition is formed from the following components. All percentages are by weight, unless specified otherwise.

| Part One | |
|---|---|
| DMS (MW 28,000) | 50.0% |
| Methylhydrosiloxane dimethylsiloxane cross-linker | 6.0% |
| Silanated 0.7 micron glass filler | 37.5% |
| Silanated nano silicone filler | 5.5% |
| Glycerin | 1.0% |
| Part Two | |
| DMS (MW 28,000) | 50.0% |
| Silanated 0.7 micron glass filler | 42.4% |
| Silanated nano silicone filler | 6.0% |
| Glycerin | 1.0% |
| Platinum-divinyltetramethylsiloxane complex | 0.1% |
| Bubblegum flavor | 0.5% |

The two parts are of relatively high viscosity so as to have a putty like consistency and are kneaded and rolled together for about 30 seconds so as to effect mixing of the two parts. The mixed composition is applied over a labial surface of a selected orthodontic bracket bonded to a tooth before polymerization is complete, and is shaped and manipulated to a desired shape and coverage of the bracket. The composition completes polymerization within about 80 seconds after initial mixing, which polymerization is completed in place on the bracket. The polymerized composition has a soft, rubbery feel, and adheres to and/or mechanically interlocks around the bracket so as to grip the bracket surface, preventing rubbing of the bracket surface against the soft inner labial tissue of the orthodontic patient. The composition has a bubblegum flavor and remains in place significantly longer than wax, and wears away and/or becomes dislodged in normal use after about 8 hours to about 2 days.

Example 4

An exemplary two part silicone composition is formed from the following components. All percentages are by weight, unless specified otherwise.

| Part One | |
| --- | --- |
| DMS (MW 28,000) | 50.0% |
| Methylhydrosiloxane dimethylsiloxane cross-linker | 6.0% |
| Silanated 0.7 micron glass filler | 37.45% |
| Silanated nano silicone filler | 5.5% |
| Glycerin | 1.0% |
| Blue colorant | 0.05% |
| Part Two | |
| DMS (MW 28,000) | 50.0% |
| Silanated 0.7 micron glass filler | 42.35% |
| Silanated nano silicone filler | 6.0% |
| Glycerin | 1.0% |
| Platinum-divinyltetramethylsiloxane complex | 0.1% |
| Bubblegum flavor | 0.5% |
| Tan colorant | 0.05% |

The two parts are of relatively high viscosity so as to have a putty like consistency. Each part is colored (blue and tan respectively) so that as they are kneaded and rolled together it is easy to see when the two parts are adequately mixed. The two parts are kneaded and rolled together for about 30 seconds so as to effect mixing of the two parts. The mixed composition is applied over a labial surface of a selected orthodontic bracket bonded to a tooth before polymerization is complete, and is shaped and manipulated to a desired shape and coverage of the bracket. The composition completes polymerization within about 80 seconds after initial mixing, which polymerization is completed in place on the bracket. The polymerized composition has a soft, rubbery feel, and adheres to and/or mechanically interlocks around the bracket so as to grip the bracket surface, preventing rubbing of the bracket surface against the soft inner labial tissue of the orthodontic patient. The composition has a bubblegum flavor and remains in place significantly longer than wax, and wears away and/or becomes dislodged in normal use after about 8 hours to about 2 days

Example 5

An exemplary two part silicone composition is formed from the following components. All percentages are by weight, unless specified otherwise.

| Part One | |
| --- | --- |
| DMS (MW 28,000) | 50.0% |
| Methylhydrosiloxane dimethylsiloxane cross-linker | 6.0% |
| Silanated 0.7 micron glass filler | 37.4% |
| Silanated nano silicone filler | 5.5% |
| Glycerin | 1.0% |
| Blue colorant | 0.1% |
| Part Two | |
| DMS (MW 28,000) | 50.0% |
| Silanated 0.7 micron glass filler | 42.4% |
| Silanated nano silicone filler | 6.0% |
| Glycerin | 1.0% |
| Platinum-divinyltetramethylsiloxane complex | 0.1% |
| Bubblegum flavor | 0.5% |

The two parts are of relatively high viscosity so as to have a putty like consistency. Part one is initially colored blue, while part one is largely colorless so that as they are kneaded and rolled together it is easy to see when the two parts are adequately mixed (there are no longer two separate colored portions). The two parts are kneaded and rolled together for about 30 seconds so as to effect mixing of the two parts. The mixed composition is applied over a labial surface of a selected orthodontic bracket bonded to a tooth before polymerization is complete, and is shaped and manipulated to a desired shape and coverage of the bracket. The composition completes polymerization within about 80 seconds after initial mixing, which polymerization is completed in place on the bracket. The polymerized composition has a soft, rubbery feel, and adheres to and/or mechanically interlocks around the bracket so as to grip the bracket surface, preventing rubbing of the bracket surface against the soft inner labial tissue of the orthodontic patient. The composition has a bubblegum flavor and remains in place significantly longer than wax, and wears away and/or becomes dislodged in normal use after about 8 hours to about 2 days

Example 6

An exemplary two part silicone composition is formed from the following components. All percentages are by weight, unless specified otherwise.

| Part One | |
| --- | --- |
| DMS (MW 28,000) | 50.0% |
| Methylhydrosiloxane dimethylsiloxane cross-linker | 6.0% |
| Silanated 0.7 micron glass filler | 36.25% |
| Silanated nano silicone filler | 5.5% |
| Glycerin | 1.0% |
| Blue colorant | 0.75% |
| Silver | 0.5% |
| Part Two | |
| DMS (MW 28,000) | 50.0% |
| Silanated 0.7 micron glass filler | 41.9% |
| Silanated nano silicone filler | 6.0% |
| Glycerin | 1.0% |
| Platinum-divinyltetramethylsiloxane complex | 0.1% |

-continued

| | |
|---|---|
| Silver | 0.5% |
| Bubblegum flavor | 0.5% |

The two parts are of relatively high viscosity so as to have a putty like consistency. Part one is initially colored blue, while part one is largely colorless so that as they are kneaded and rolled together it is easy to see when the two parts are adequately mixed (there are no longer two separate colored portions). The two parts are kneaded and rolled together for about 30 seconds so as to effect mixing of the two parts. The mixed composition is applied over a labial surface of a selected orthodontic bracket bonded to a tooth before polymerization is complete, and is shaped and manipulated to a desired shape and coverage of the bracket. The composition completes polymerization within about 80 seconds after initial mixing, which polymerization is completed in place on the bracket. The polymerized composition has a soft, rubbery feel, and adheres to and/or mechanically interlocks around the bracket so as to grip the bracket surface, preventing rubbing of the bracket surface against the soft inner labial tissue of the orthodontic patient. The composition has a bubblegum flavor and remains in place significantly longer than wax, and wears away and/or becomes dislodged in normal use after about 8 hours to about 2 days Example 7

An exemplary two part silicone composition is formed from the following components. All percentages are by weight, unless specified otherwise.

| Part One | |
|---|---|
| DMS (MW 17,000) | 40.0% |
| Methylhydrosiloxane dimethylsiloxane cross-linker | 6.0% |
| Silanated 0.7 micron glass filler | 47.5% |
| Silanated nano silicone filler | 5.5% |
| Glycerin | 1.0% |
| Part Two | |
| DMS (MW 17,000) | 40.0% |
| Silanated 0.7 micron glass filler | 50.9% |
| Silanated nano silicone filler | 6.0% |
| Glycerin | 1.0% |
| Platinum-divinyltetramethylsiloxane complex | 0.1% |
| Bubblegum flavor | 2% |

The two parts are of relatively high viscosity so as to have a putty like consistency and are kneaded and rolled together for about 30 seconds so as to effect mixing of the two parts. The mixed composition is applied over a labial surface of a selected orthodontic bracket bonded to a tooth before polymerization is complete, and is shaped and manipulated to a desired shape and coverage of the bracket. The composition completes polymerization within about 80 seconds after initial mixing, which polymerization is completed in place on the bracket. The polymerized composition has a soft, rubbery feel, and adheres to and/or mechanically interlocks around the bracket so as to grip the bracket surface, preventing rubbing of the bracket surface against the soft inner labial tissue of the orthodontic patient. The composition has a bubblegum flavor and remains in place significantly longer than wax, and wears away and/or becomes dislodged in normal use after about 8 hours to about 2 days Example 8

An exemplary two part silicone composition is formed from the following components. All percentages are by weight, unless specified otherwise.

| Part One | |
|---|---|
| DMS (MW 63,000) | 55.0% |
| Methylhydrosiloxane dimethylsiloxane cross-linker | 6.0% |
| Silanated 0.7 micron glass filler | 32.5% |
| Silanated nano silicone filler | 5.5% |
| Glycerin | 1.0% |
| Part Two | |
| DMS (MW 63,000) | 55.0% |
| Silanated 0.7 micron glass filler | 35.9% |
| Silanated nano silicone filler | 6.0% |
| Glycerin | 1.0% |
| Platinum-divinyltetramethylsiloxane complex | 0.1% |
| Bubblegum flavor | 2% |

Figure 2:
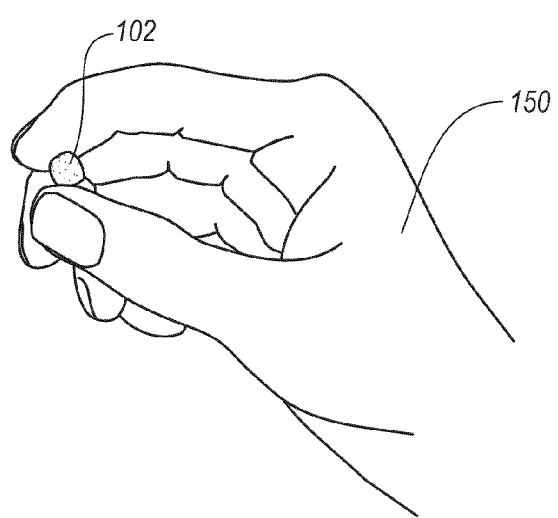
FIG. 2 shows the person kneading and/or rolling the two separate parts together so as to cause them to mix together.

The two parts are of relatively high viscosity so as to have a putty like consistency and are kneaded and rolled together for about 30 seconds so as to effect mixing of the two parts. The mixed composition is applied over a labial surface of a selected orthodontic bracket bonded to a tooth before polymerization is complete, and is shaped and manipulated to a desired shape and coverage of the bracket. The composition completes polymerization within about 80 seconds after initial mixing, which polymerization is completed in place on the bracket. The polymerized composition has a soft, rubbery feel, and adheres to and/or mechanically interlocks around the bracket so as to grip the bracket surface, preventing rubbing of the bracket surface against the soft inner labial tissue of the orthodontic patient. The composition has a bubblegum flavor and remains in place significantly longer than wax, and wears away and/or becomes dislodged in normal use after about 8 hours to about 2 days IV. Exemplary Methods of Use FIG. 1 illustrates a dual barrel syringe 100 being used to dispense a two-part polymerizable temporary coating composition onto the finger tips of a user 150. Because both parts of the composition initially have a putty-like consistency, parts 102a and 102b are initially dispensed separately, and mixing of the composition so as to form a substantially homogeneous composition is performed by the user 150. For example, as shown in FIG. 2, the user may knead and/or roll the two separate parts together so as to cause the two parts to mix together, forming a silicone temporary coating composition 102.

Upon mixing of the two parts 102a and 102b, polymerization begins to occur. Typically, the composition may be mixed by kneading and/or rolling the two parts together between the user's fingertips for a short period, after which the composition is placed over an orthodontic wire or bracket, before polymerization is complete. Typically, substantial mixing is achieved within about 5-20 seconds of beginning rolling and/or kneading, which allows the user some time to position the mixed coating composition over one or more selected brackets and/or wires, and press and/or mold the composition as desired before polymerization is substantially complete. Polymerization is substantially complete after about 10 seconds to about 3 minutes, more typically from about 30 seconds to about 2 minutes, most typically from about 45 seconds to about 90 seconds. Once polymerization is complete, the composition holds to the bracket, wire, or other intra-oral device surface where applied by adhesion and/or by a mechanical interlock as the result of the user molding the material so as to clasp and grip around the desired surface. In other words, some compositions may chemically adhere to the underlying substrate surface, while others may rely on a physical mechanical interlocking grip around the bracket or other device or portion thereof to hold the composition in place. The nature of the mechanism by which the composition is held in place depends on the characteristics of the selected composition as well as the substrate.

Figure 3:
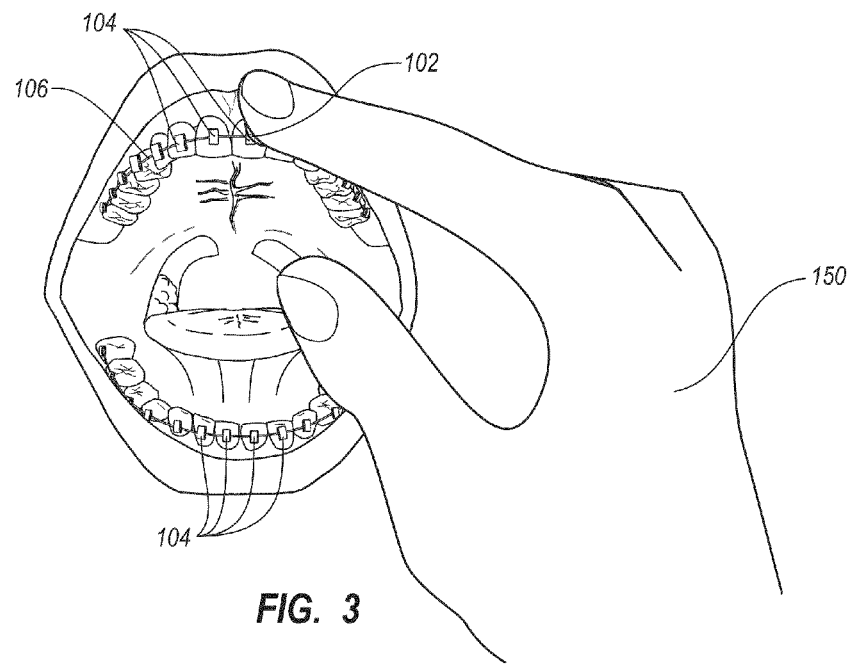
FIG. 3 shows the person applying a portion of the mixed temporary coating composition in a partially polymerized state over one or more orthodontic brackets and/or arch wires within the person's mouth.
Figure 4:
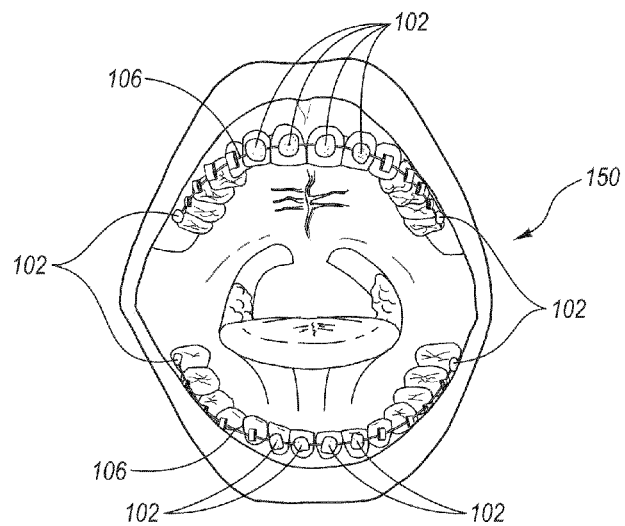
FIG. 4 is a perspective view of the person's opened mouth once the silicone temporary coating composition has been applied over selected portions of orthodontic brackets and/or wires (e.g., the incisor brackets and the terminal brackets/arch wire ends).

As shown in FIGS. 3-4, the user may separate a portion of the composition from the kneaded and/or rolled mass of temporary coating composition 102 (or apply the whole mass) and press the composition 102 so as to cover a selected bracket, wire, another intra-oral device, or portion thereof. For example, a user may typically place the polymerizable temporary coating composition 102 over the brackets 104 on the upper and lower incisors, and on the terminal brackets which may cover or only partially cover the wire ends of arch wire 106. Although these locations (incisor brackets and terminal wire ends/terminal brackets) are the most likely locations to which the composition 102 is applied relative to an orthodontic appliance system, the composition may be applied over any bracket or arch wire surface, or over any other intra-oral device, as desired by the user. Advantageously, the silicone temporary coating composition 102 completes polymerization in place, over a selected bracket or wire, which results in the composition 102 adhering or otherwise holding to (e.g., by mechanical interlock) the underlying bracket or wire relatively strongly. In other words, because the temporary coating composition polymerizes in place, it holds much more strongly to the substrate where placed as compared to traditionally used wax, allowing the user to apply the material with significantly less frequency.

Furthermore, no active step is required of the user in order to remove the temporary coating material, as it wears away as a result of exposure to saliva, movement of the tongue, and other forces present within the mouth. Advantageously the temporary coating composition as described has been found by the present inventors to remain substantially adhered over brackets and/or wires under typical conditions for a period of about 8 hours to about 5 days, more typically from about 12 hours to about 4 days, and most typically from about 1 and about 3 days. In other words, in one embodiment the composition may remain adhered for at least about 8 hours, more preferably at least about 1 day, and most preferably at least about 2 days. Because the composition passively wears away and/or becomes dislodged (e.g., after no more than about 3-5 days), no additional action is required of the user, as would be required with a device which for example, may be fitted over brackets and/or wire ends so as to prevent chaffing of the soft oral tissues and/or pokes from the wires. This short time period provides time for the soft oral tissue to callous and thicken so as to no longer be irritated by adjacent brackets and/or wires. The absence of the material at this stage (i.e., once the soft tissues have calloused/thickened) is an advantage relative to devices fitted over the brackets and/or wire ends, as it is much more comfortable for the patient.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for in-situ temporary coating of at least one intra-oral device so as to reduce discomfort to surrounding soft tissues of the oral cavity comprising the steps of:
   providing at least one intra-oral device installed within an oral cavity of a person;
   mixing a two-part polymerizable composition, the two-part polymerizable composition including a polymerizable component and an initiator system for initiating polymerization such that a first part and a second part of the two-part composition begin to polymerize upon mixing of the first and second parts so as to form a polymerizable temporary coating composition, wherein the two-part polymerizable composition further comprises at least one of a filler or plasticizer and wherein the polymerizable temporary coating composition is configured so that, after polymerization, it spontaneously wears away over time from a surface of the intra-oral device to which it is applied and after a person's soft oral tissues have adjusted to the presence of the intra-oral device; and
   applying the polymerizable temporary coating composition to an accessible surface of the at least one installed intra-oral device before the polymerizable temporary coating composition has substantially completed polymerization such that the coating composition holds to the intra-oral device where applied and, after polymerization, spontaneously wears away over time from the intra-oral device once a person's soft oral tissues have adjusted to the presence of the intra-oral device.

2. A method as recited in claim 1, wherein the polymerizable component is selected from the group consisting of a urethane, an epoxy, a polymerizable siloxane, and combinations thereof.

3. A method as recited in claim 1, wherein the first and second parts of the two-part polymerizable temporary coating composition have a consistency of a putty, the step of mixing the first part with the second part comprising kneading and/or rolling the two parts together.

4. A method as recited in claim 3, wherein applying the polymerizable temporary coating composition comprises molding and/or pressing the polymerizable temporary coating composition over and/or around the accessible surface of at least one intra-oral device before the polymerizable temporary coating composition has substantially completed polymerization.

5. A method as recited in claim 3, wherein the polymerizable temporary coating composition substantially completes polymerization within a range between about 10 seconds and about 3 minutes after beginning kneading and/or rolling of the two parts together.

6. A method as recited in claim 3, wherein the polymerizable temporary coating composition substantially completes polymerization within a range between about 30 seconds and about 2 minutes after beginning kneading and/or rolling of the two parts together.

7. A method as recited in claim 3, wherein the polymerizable temporary coating composition substantially completes polymerization within a range between about 45 seconds and about 90 seconds after beginning kneading and/or rolling of the two parts together.

8. A method as recited in claim 1, wherein the coating composition, after polymerization, spontaneously wears away from the surface of the intra-oral device in a period of time of less than 5 days.

9. A method as recited in claim 1, wherein the polymerizable temporary coating composition further comprises a colorant.

10. A method as recited in claim 1, wherein the polymerizable temporary coating composition further comprises a flavorant.

11. A method for in-situ temporary coating of at least one intra-oral device so as to reduce discomfort to surrounding soft tissues of the oral cavity comprising the steps of:
providing at least one intra-oral device installed on one or more teeth within an oral cavity of a person;
mixing a two-part composition, the two-part composition including a vinyl siloxane component, a cross-linking component, and a catalyst activator such that a first part and a second part of the two-part composition begin to polymerize upon mixing of the first and second parts so as to form a silicone temporary coating composition, wherein the two-part polymerizable composition further comprises at least one of a filler or plasticizer and wherein the polymerizable temporary coating composition is configured so that, after polymerization, it spontaneously wears away over time from a surface of the intra-oral device to which it is applied and after a person's soft oral tissues have adjusted to the presence of the intra-oral device; and
applying the silicone temporary coating composition to an accessible surface of the at least one installed intra-oral device before the silicone temporary coating composition has substantially completed polymerization such that the coating composition holds to the intra-oral device where applied and, after polymerization, spontaneously wears away over time from the intra-oral device once a person's soft oral tissues have adjusted to the presence of the intra-oral device.

12. A method as recited in claim 11, wherein the first and second parts of the two-part silicone temporary coating composition have a consistency of a putty, the step of mixing the first part with the second part comprising kneading and/or rolling the two parts together.

13. A method as recited in claim 12, further comprising molding and/or pressing the silicone temporary coating composition over and/or around a surface of at least one intra-oral device before the silicone temporary coating composition has substantially completed polymerization.

14. A method as recited in claim 12, wherein the silicone temporary coating composition substantially completes polymerization within a range between about 10 seconds and about 3 minutes after beginning kneading and/or rolling of the two parts together.

15. A method as recited in claim 12, wherein the silicone temporary coating composition substantially completes polymerization within a range between about 30 seconds and about 2 minutes after beginning kneading and/or rolling of the two parts together.

16. A method as recited in claim 12, wherein the silicone temporary coating composition substantially completes polymerization within a range between about 45 seconds and about 90 seconds after beginning kneading and/or rolling of the two parts together.

17. A method as recited in claim 11, wherein a substantial portion of the silicone temporary coating composition holds to the surface of the intra-oral device for at least 8 hours.

18. A method as recited in claim 11, wherein a substantial portion of the silicone temporary coating composition holds to the surface of the intra-oral device for at least 1 day.

19. A method as recited in claim 11, wherein a substantial portion of the silicone temporary coating composition holds to the surface of the intra-oral device for at least 2 days.

20. A method as recited in claim 11, wherein the silicone temporary coating composition, after polymerization, spontaneously wears away from the surface of the intra-oral device in a period of time of less than 5 days.

21. A system for use by a patient in in-situ temporary coating of one or more intra-oral devices that are designed to be attached to one or more teeth of a person so as to reduce discomfort to surrounding soft tissues of the oral cavity comprising:
at least one orthodontic intra-oral device designed to be attached to one or more teeth of a person, the intra-oral device being rigid so as to irritate soft, sensitive oral tissues once installed; and
a two-part silicone temporary coating composition comprising a first part and a second part, the two-part silicone temporary coating composition comprising:
a vinyl siloxane component, a cross-linking component, and a catalyst activator,
wherein at least one of the vinyl siloxane component, the cross-linking component, or the catalyst activator is initially contained within a first part that is separate from at least one other of the vinyl siloxane component, the cross-linking component, or the catalyst activator contained within the second part, and
wherein the first part and the second part begin to polymerize upon mixing of the first part with the second part and form a polymerized vinyl siloxane temporary coating composition that is configured so as to spontaneously wear away over time from a surface of the orthodontic intra-oral device to which it is applied during use.

22. A system as recited in claim 21, wherein the first and second parts of the silicone temporary coating composition each have a consistency of a putty.

23. A system as recited in claim 21, wherein the vinyl siloxane component comprises dimethyl siloxane having a molecular weight between about 25,000 and about 300,000.

24. A system as recited in claim 21, wherein the at least one orthodontic intra-oral device comprises at least one of an orthodontic bracket or an orthodontic arch wire and the two-part silicone temporary coating composition has a formulation so that, when it is mixed and applied over the orthodontic bracket and/or orthodontic arch wire and has polymerized, it will spontaneously wear away and/or become dislodged in a period of time of less than 5 days.

25. A system as recited in claim 21, wherein the at least one intra-oral device comprises at least one of an orthodontic bracket or an arch wire.

26. A method for in-situ temporary coating of at least one intra-oral device so as to reduce discomfort to surrounding soft tissues of the oral cavity comprising the steps of:
providing at least one intra-oral device installed within an oral cavity of a person;
mixing a two-part polymerizable composition, the two-part polymerizable composition including a polymerizable component and an initiator system for initiating polymerization such that a first part and a second part of the two-part composition begin to polymerize upon mixing of the first and second parts so as to form a polymerizable temporary coating composition that, when polymerized, will spontaneously wear away over time from a surface of the intra-oral device to which it is applied once a person's soft oral tissues have adjusted to the presence of the intra-oral device;

applying the coating composition to an accessible surface of the at least one installed intra-oral device before the polymerizable temporary coating composition has substantially completed polymerization such that the coating composition holds to the intra-oral device where applied and, after polymerization, spontaneously wears away over time from the intra-oral device once a person's soft oral tissues have adjusted to the presence of the intra-oral device; and wherein the polymerizable component comprises at least one of a urethane or an epoxy.

27. A method for in-situ temporary coating of at least one intra-oral device so as to reduce discomfort to surrounding soft tissues of the oral cavity comprising the steps of:

providing at least one intra-oral device installed within an oral cavity of a person;

mixing a two-part polymerizable composition, the two-part polymerizable composition including a polymerizable component and an initiator system for initiating polymerization such that a first part and a second part of the two-part composition begin to polymerize upon mixing of the first and second parts so as to form a polymerizable temporary coating composition that, when polymerized, will spontaneously wear away over time from a surface of the intra-oral device to which it is applied once a person's soft oral tissues have adjusted to the presence of the intra-oral device;

applying the coating composition to an accessible surface of the at least one installed intra-oral device before the polymerizable temporary coating composition has substantially completed polymerization such that the coating composition holds to the intra-oral device where applied and, after polymerization, spontaneously wears away over time from the intra-oral device once a person's soft oral tissues have adjusted to the presence of the intra-oral device; and wherein each part of the two-part polymerizable temporary coating composition comprises a colorant, the colorant within the first part being different from the colorant within the second part.

28. A system as recited in claim 21, wherein the polymerized vinyl siloxane temporary coating composition is configured to spontaneously wear away over time from the surface of the intra-oral device in a period of time of less than 5 days.

* * * * *

UNITED STATES PATENT AND TRADEMARK OFFICE
CERTIFICATE OF CORRECTION

| | |
|---|---|
| PATENT NO. | : 8,075,307 B2 |
| APPLICATION NO. | : 12/237194 |
| DATED | : December 13, 2011 |
| INVENTOR(S) | : Jessop et al. |

It is certified that error appears in the above-identified patent and that said Letters Patent is hereby corrected as shown below:

Column 4
Line 50, change "suitable soft," to --suitable, soft,--
Line 54, change "absent application" to --absent of application--

Column 7
Line 44, change "achieved" to --achieve--

Column 9
Line 49, change "effect" to --affect--

Column 10
Line 24, change "effect" to --affect--
Line 64, change "effect" to --affect--

Column 11
Line 46, change "effect" to --affect--
Line 66, change "days" to --days.--

Column 12
Line 29, change "effect" to --affect--
Line 44, change "days" to --days.--

Column 13
Line 12, change "effect" to --affect--
Line 26, change "days" to --days.--
Line 52, change "effect" to --affect--
Line 67, change "days" to --days.--

Signed and Sealed this
Eighth Day of May, 2012

David J. Kappos
*Director of the United States Patent and Trademark Office*

CERTIFICATE OF CORRECTION (continued)
U.S. Pat. No. 8,075,307 B2

Column 14
Line 25, change "effect" to --affect--
Line 39, change "days" to --days.--

Column 15
Line 51, change "which for" to --which, for--
Line 52, change "chaffing" to --chafing--

Column 16
Line 24, change "of the at" to --of at--

Column 17
Line 28, change "of the at" to --of at--

Column 18
Line 41, change "wherein the at" to --wherein at--
Line 49, change "wherein the at" to --wherein at--

Column 19
Line 2, change "of the at" to --of at--

Column 20
Line 6, change "of the at" to --of at--